(12) United States Patent
Liu et al.

(10) Patent No.: US 12,187,688 B2
(45) Date of Patent: Jan. 7, 2025

(54) CRYSTAL FORM OF TETRAMETHYLPYRAZINE NITRONE, PREPARATION METHOD AND USE THEREOF

(71) Applicant: GUANGZHOU MAGPIE PHARMACEUTICALS CO., LTD., Guangdong (CN)

(72) Inventors: Wei Liu, Guangzhou (CN); Yewei Sun, Guangzhou (CN); Yuqiang Wang, Guangzhou (CN)

(73) Assignee: GUANGZHOU MAGPIE PHARMACEUTICALS CO., LTD., Guangzhou (CN)

( * ) Notice: Subject to any disclaimer, the term of this patent is extended or adjusted under 35 U.S.C. 154(b) by 612 days.

(21) Appl. No.: 17/600,915

(22) PCT Filed: Jul. 31, 2019

(86) PCT No.: PCT/CN2019/098724
§ 371 (c)(1),
(2) Date: Oct. 1, 2021

(87) PCT Pub. No.: WO2020/199440
PCT Pub. Date: Oct. 8, 2020

(65) Prior Publication Data
US 2022/0153707 A1    May 19, 2022

(30) Foreign Application Priority Data
Apr. 1, 2019 (CN) .......................... 201910255805.3

(51) Int. Cl.
C07D 241/12    (2006.01)
A61K 31/4965    (2006.01)

(52) U.S. Cl.
CPC ........ *C07D 241/12* (2013.01); *C07B 2200/13* (2013.01)

(58) Field of Classification Search
CPC .......................... C07D 241/12; A61K 31/4965
USPC ........................................ 544/410; 514/252.1
See application file for complete search history.

(56) References Cited

FOREIGN PATENT DOCUMENTS

| CN | 101468970 A | 7/2009 |
|---|---|---|
| CN | 104803880 A | 7/2015 |
| CN | 105963298 A | 9/2016 |
| CN | 107157999 A | 9/2017 |

OTHER PUBLICATIONS

Sun et al.; "Antioxidative and thrombolytic TMP nitrone for treatment of ischemic stroke;" Bioorganic & Medicinal Chemistry; 2008; pp. 8868-8874; vol. 16.

Dec. 27, 2019 Search Report issued in International Patent Application No. PCT/CN2019/098724.

*Primary Examiner* — Charanjit Aulakh
(74) *Attorney, Agent, or Firm* — Oliff PLC

(57) ABSTRACT

A crystal form of tetramethylpyrazine nitrone (TBN), and a preparation method and use thereof is provided. A crystal form A of TBN has characteristic diffraction peaks in the XRPD pattern at 2θ°: 10.60±0.2, 11.03±0.2, 15.31±0.2, 15.55±0.2, 17.14±0.2, 17.93±0.2, and 23.81±0.2. The crystal form A has low risk of polymorphism transformation and good stability, which contribute to the stability of the preparations during the production and storage processes, and effectively guarantee the consistency of the content of the crystal form in the preparations. Therefore, the preparations are safe, effective, and controllable in quality. Also, the crystal form A has high biological activity, good druggability, and high bioavailability, fast onset of action.

10 Claims, 20 Drawing Sheets

CRYSTAL FORM OF TETRAMETHYLPYRAZINE NITRONE, PREPARATION METHOD AND USE THEREOF

TECHNICAL FIELD

The present invention relates to the field of pharmaceutical chemistry, and in particular to a crystal form of tetramethylpyrazine nitrone, and a preparation method and use thereof.

BACKGROUND

Tetramethylpyrazine nitrone, abbreviated as TBN, is a nitrone derivative of tetramethylpyrazine (TMP), and a new compound chemically synthesized by adding a nitrone pharmacophore to the structure of tetramethylpyrazine. It has a chemical name of (Z)-2-methyl-N-((3,5,6-trimethylpyrazin-2-yl)methylene)propan-2-amine oxide, a molecular formula of $C_{12}H_{19}N_3O$, a molecular weight of 221.30, and a chemical structure shown below:

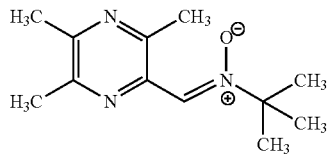 [SMILES: Cc1nc(C)c(/C=[N+](\[O-])C(C)(C)C)nc1C]

Structural Formula of Tetramethylpyrazine Nitrone (TBN)

TBN can inhibit the oxidative damage of nerve cells caused by ischemia, thereby protecting the nerve cells and alleviating the neurological symptoms and dysfunctions associated with cerebral embolism. It can be used clinically in the treatment of neurological diseases, cardiovascular and cerebrovascular diseases, and aging-associated degenerative diseases.

SUMMARY

The present invention aims to provide a crystal form of TBN, and a preparation method and use thereof.

A first object of the present invention is to provide a crystal form A of TBN, having characteristic diffraction peaks in the XRPD pattern of the crystal form at 2θ°: 10.60±0.2, 11.03±0.2, 15.31±0.2, 15.55±0.2, 17.14±0.2, 17.93±0.2, and 23.81±0.2.

In a specific embodiment, the crystal form A of TBN has characteristic diffraction peaks in the XRPD pattern of the crystal form at 2θ°: 10.60±0.2, 11.03±0.2, 13.51±0.2, 15.31±0.2, 15.55±0.2, 17.14±0.2, 17.93±0.2, 21.22±0.2, 23.81±0.2, 25.23±0.2, and 27.08±0.2.

In a specific embodiment, the crystal form A of TBN has basically the same XRPD pattern as shown in FIG. 1.

Further, the crystal form A of TBN according to the present invention has needle-, cube-, or rod-shaped crystalline structure, as shown in the micrographs of FIGS. 5 and 6.

Further, the melting point of the crystal form A of TBN is 76-78° C., respectively.

Further, the DSC profile of the crystal form A of TBN is basically as shown in FIG. 3.

Further, the TGA pattern of the crystal form A of TBN is shown in FIG. 7.

Further, the present invention provides an infrared spectrum of the crystal form A of TBN, as shown in FIG. 9.

In the present invention, a systematic crystal form screening experiment is carried out by using a screening method including evaporative crystallization (single solvent method and mixed solvent method), hot dissolution-cold precipitation, and suspension beating. The screening involves solvents such as tetrahydrofuran, ethyl acetate, toluene, acetone, dioxane, isopropanol, petroleum ether, n-hexane, isopropyl acetate, isooctane and isobutyl acetate, and the screening results all reveal crystal form A.

Further, the present invention also provides a method for preparing the crystal form A of TBN, which includes the following steps:

(1) mixing the API (active pharmaceutical ingredient) TBN with an organic solvent, heating in a water bath to 60-80° C., stirring and filtering, and cooling the filtrate for crystallization to obtain a crystalline solid; and (2) mixing the crystalline solid obtained in Step (1) and n-heptane, heating to dissolve it, and cooling for crystallization to obtain the crystal form A of TBN.

Further, in the preparation method of the present invention, the organic solvent in Step (1) is one or more selected from ethyl acetate, n-hexane, n-heptane and cyclohexane, and further preferably, n-hexane or n-heptane, or a mixed solvent of n-hexane and ethyl acetate. The applicant finds that the use of a preferred organic solvent can significantly reduce the impurity content.

Further, in the preparation method of the present invention, the weight-to-volume ratio of the API TBN to the organic solvent in Step (1) is 1:5-20, and preferably 1:8-12.

Further, in the preparation method of the present invention, the temperature of cooling for crystallization in Step (1) is 2-12° C., more preferably 3-10° C., and most preferably 3-5° C. The applicant finds that in the most preferred range, the impurity content can be significantly reduced.

Further, in the preparation method of the present invention, the weight-to-volume ratio of API TBN to n-heptane in Step (2) is preferably 1:1-5, and most preferably 1:1-3.

Further, in the preparation method of the present invention, the mixing and heating temperature of the crystalline solid and n-heptane in Step (2) is 60-80° C., and preferably 65-75° C.

Further, in the preparation method of the present invention, the temperature of cooling for crystallization in Step (2) is 2-12° C., and more preferably 4-10° C.

A second object of the present invention is to provide a TBN dihydrate, having characteristic diffraction peaks in the XRPD pattern at 2θ°: 8.91±0.2, 11.46±0.2, 14.29±0.2, 17.60±0.2, 21.19±0.2, 22.02±0.2, 23.19±0.2, 24.30±0.2, 24.92±0.2, 29.20±0.2, and 31.41±0.2.

In a specific embodiment, the TBN dihydrate has characteristic diffraction peaks in the XRPD pattern at 2θ°: 8.91±0.2, 11.46±0.2, 12.00±0.2, 14.29±0.2, 17.60±0.2, 19.50±0.2, 21.19±0.2, 22.02±0.2, 23.19±0.2, 24.30±0.2, 24.92±0.2, 26.70±0.2, 29.20±0.2, 31.41±0.2, and 36.20±0.2.

In a specific embodiment, the TBN dihydrate has basically the same XRPD pattern as shown in FIG. 2.

Further, the melting point of the TBN dihydrate is 37-40° C.

Further, the DSC profile of the TBN dihydrate is basically as shown in FIG. 4.

Further, the TGA pattern of the TBN dihydrate is shown in FIG. 8.

When the TBN dihydrate according to the present invention reaches the melting point (about 37-40° C.), the weight begins to decrease, and the weight loss is 13.67%.

The TBN dihydrate according to the present invention is obtained by cold precipitation of TBN in a binary system of a saturated ethanol-water solution, where preferably the content of ethanol in percentages by weight in the ethanol-water solution is 5-50%, and further preferably 5-20%.

In another aspect, the present invention provides a pharmaceutical composition comprising one or more of the crystal form A or dihydrate of the present invention. The pharmaceutical composition may also optionally comprise a pharmaceutically acceptable carrier, excipient, filler, binder, disintegrant, glidant and/or medium, etc.

On the other hand, the crystal form A and/or dihydrate of the present invention, or the pharmaceutical composition of the present invention can be given by oral administration or injection or other routes of administration.

In another aspect, the present invention also provides a dosage form comprising the crystal form A and/or dihydrate of the present invention, including but not limited to tablets, capsules, powder injections, and dispersions, etc., preferably tablets and powder injections.

In another aspect, the present invention also provides use of the crystal form A and/or dihydrate or pharmaceutical composition of the present invention in the preparation of drugs for the treatment of neurological diseases, cardiovascular and cerebrovascular diseases and aging-related degenerative diseases.

The present invention has the following beneficial effects.

(1) The preparation method of the crystal form A of TBN and the TBN dihydrate described in the present invention is simple and easy for industrial production.

(2) The crystal form A of TBN according to the present invention is stable in the heat treatment, mechanical treatment and acceleration (50° C., 75% RH), is at low risk of polymorphism transformation, and has good stability, which contribute to the stability of the preparations during the production and storage processes, and effectively guarantee the consistency of the content of the crystal form in the preparations. Therefore, the preparations are safe, effective, and controllable in quality.

(3) The crystal form A of TBN according to the present invention is readily soluble in most solvents (such as acetonitrile, methanol, ethanol, acetone and ethyl acetate, etc.) and very soluble in water, and has high biological activity, good druggability, high bioavailability, fast onset of action, and high biological activity.

DETAILED DESCRIPTION

Figure 1:
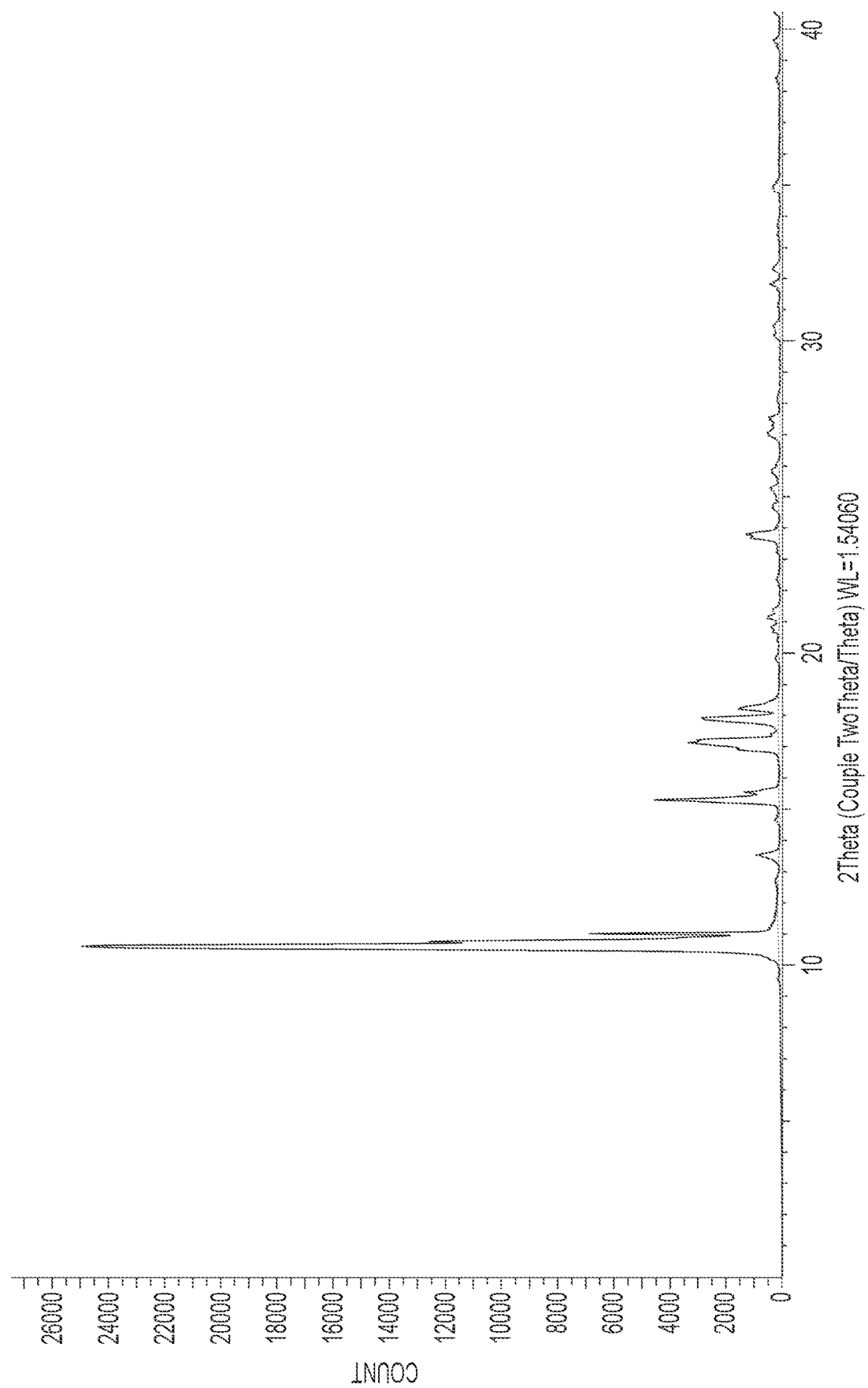
FIG. 1 shows an XRD pattern of the crystal form A of TBN.

The present invention will be further described by way of examples. It should be understood that the specific examples described herein are merely provided for illustrating, instead of limiting the present invention. Any simple modifications can be made to the preparation method of the present invention without departing from the concept of the present invention, which all fall within the protection scope of the present invention. In the examples where no specific conditions are indicated for the experimental procedures, generally known means are employed. Test materials used in the following examples are commercially available, unless otherwise specified.

In the following examples and accompanying drawings, unless otherwise specified, TBN represents TBN according to the present invention.

The characteristic diffraction peaks in the XRD patterns of the crystal form A of TBN and the TBN dihydrate in the following examples are measured under the following experimental conditions:

The instrument is X-ray powder diffraction analyzer (Bruker D2PHASER), the voltage and tube current are 30 KV and 10 mA, respectively, the 2θ scanning angle of the sample is from 3°-40°, and the scanning step is 0.02°.

Example 1

To a 250 ml round-bottom flask, API TBN (10 g), cyclohexane (100 ml) and ethyl acetate (2 ml) were added, stirred continuously at a rotation speed adjusted to 140±5 rpm, and heated in a water bath at 70° C. The solution was filtered while hot to obtain an orange-yellow solution. The filtrate was allowed to stand and cool to ambient temperature (10° C.), and then stood in a freezer at 4° C. and filtered. The filter cake was washed with n-hexane, and the solvent was removed under reduced pressure to obtain a pale yellow crystalline solid.

To a 250 ml round-bottom flask, the above crude solid TBN and 2 volumes of n-heptane were added, stirred continuously at a rotation speed adjusted to 140±5 rpm, and heated in a water bath at 70° C., to obtain an orange-yellow clear solution. The water bath was removed, and the solution was continuously stirred, cooled to 10° C. for crystallization, and filtered with suction. The solid was washed with n-heptane, and dried for 24 hrs at 38° C. under vacuum to a drying loss of <1.0%, to obtain the crystal form A of TBN.

Example 2

To a 250 ml round-bottom flask, API TBN (10 g), n-hexane (100 ml) and ethyl acetate (2 ml) were added, stirred continuously at a rotation speed adjusted to 140±5 rpm, and heated in a water bath at 70° C. The solution was filtered while hot to obtain an orange-yellow solution. The filtrate was allowed to stand and cool to ambient temperature (10° C.), and then stand in a freezer at 4° C. and filtered. The filter cake was washed with n-hexane, and the solvent was removed under reduced pressure to obtain a pale yellow crystalline solid.

To a 250 ml round-bottom flask, the above crude solid TBN and 2 volumes of n-heptane were added, stirred continuously at a rotation speed adjusted to 140±5 rpm, and heated in a water bath at 70° C., to obtain an orange-yellow clear solution. The water bath was removed, and the solution was continuously stirred, cooled to 10° C. for crystallization, and filtered with suction. The solid was washed with n-heptane, and dried for 24 hrs at 38° C. under vacuum to a drying loss of <1.0%, to obtain the crystal form A of TBN.

Example 3

To a 250 ml round-bottom flask, API TBN (10 g) and cyclohexane (100 ml) were added, stirred continuously at a rotation speed adjusted to 140±5 rpm, and heated in a water bath at 70° C. The solution was filtered while hot to obtain an orange-yellow solution. The filtrate was allowed to stand and cool to ambient temperature (10° C.), and then stood in a freezer at 4° C. and filtered. The filter cake was washed with n-hexane, and the solvent was removed under reduced pressure to obtain a pale yellow crystalline solid.

To a 250 ml round-bottom flask, the above crude solid TBN and 2 volumes of n-heptane were added, stirred continuously at a rotation speed adjusted to 140±5 rpm, and heated in a water bath at 70° C., to obtain an orange-yellow clear solution. The water bath was removed, and the solution was continuously stirred, cooled to 10° C. for crystallization, and filtered with suction. The solid was washed with n-heptane, and dried for 24 hrs at 38° C. under vacuum to a drying loss of <1.0%, to obtain the crystal form A of TBN.

Example 4

To a 250 ml round-bottom flask, API TBN (10 g) and n-hexane (100 ml) were added, stirred continuously at a rotation speed adjusted to 140±5 rpm, and heated in a water bath at 70° C. The solution was filtered while hot to obtain an orange-yellow solution. The filtrate was allowed to stand and cool to ambient temperature (10° C.), and then stood in a freezer at 4° C. and filtered. The filter cake was washed with n-hexane, and the solvent was removed under reduced pressure to obtain a pale yellow crystalline solid.

To a 250 ml round-bottom flask, the above crude solid TBN and 2 volumes of n-heptane were added, stirred continuously at a rotation speed adjusted to 140±5 rpm, and heated in a water bath at 70° C., to obtain an orange-yellow clear solution. The water bath was removed, and the solution was continuously stirred, cooled to 10° C. for crystallization, and filtered with suction. The solid was washed with n-heptane, and dried for 24 hrs at 38° C. under vacuum to a drying loss of <1.0%, to obtain the crystal form A of TBN.

Example 5

To a 250 ml round-bottom flask, API TBN (10 g) and n-heptane (100 ml) were added, stirred continuously at a rotation speed adjusted to 140±5 rpm, and heated in a water bath at 70° C. The solution was filtered while hot to obtain an orange-yellow solution. The filtrate was allowed to stand and cool to ambient temperature (10° C.), and then stood in a freezer at 4° C. and filtered. The filter cake was washed with n-hexane, and the solvent was removed under reduced pressure to obtain a pale yellow crystalline solid.

To a 250 ml round-bottom flask, the above crude solid TBN and 2 volumes of n-heptane were added, stirred continuously at a rotation speed adjusted to 140±5 rpm, and heated in a water bath at 70° C., to obtain an orange-yellow clear solution. The water bath was removed, and the solution was continuously stirred, cooled to 10° C. for crystallization, and filtered with suction. The solid was washed with n-heptane, and dried for 24 hrs at 38° C. under vacuum to a drying loss of <1.0%, to obtain the crystal form A of TBN.

Example 6

To a 250 ml round-bottom flask, API TBN (10 g) and n-hexane (100 ml) were added, stirred continuously at a rotation speed adjusted to 140±5 rpm, and heated in a water bath at 70° C. The solution was filtered while hot to obtain an orange-yellow solution. The filtrate was allowed to stand and cool to ambient temperature (10° C.), and then stood in a freezer at 10° C. and filtered. The filter cake was washed with n-hexane, and the solvent was removed under reduced pressure to obtain a pale yellow crystalline solid.

To a 250 ml round-bottom flask, the above crude solid TBN and 2 volumes of n-heptane were added, stirred continuously at a rotation speed adjusted to 140±5 rpm, and heated in a water bath at 70° C., to obtain an orange-yellow clear solution. The water bath was removed, and the solution was continuously stirred, cooled to 10° C. for crystallization, and filtered with suction. The solid was washed with n-heptane, and dried for 24 hrs at 38° C. under vacuum to a drying loss of <1.0%, to obtain the crystal form A of TBN.

Example 7

To a 250 ml round-bottom flask, API TBN (10 g) and n-hexane (100 ml) were added, stirred continuously at a rotation speed adjusted to 140±5 rpm, and heated in a water bath at 70° C. The solution was filtered while hot to obtain an orange-yellow solution. The filtrate was allowed to stand and cool to ambient temperature (10° C.), and then stood in a freezer at 4° C. and filtered. The filter cake was washed with n-hexane, and the solvent was removed under reduced pressure to obtain a pale yellow crystalline solid.

To a 250 ml round-bottom flask, the above crude solid TBN and 2 volumes of n-heptane were added, stirred continuously at a rotation speed adjusted to 140±5 rpm, and heated in a water bath at 70° C., to obtain an orange-yellow clear solution. The water bath was removed, and the solution was continuously stirred, cooled to 10° C. for crystallization, and filtered with suction. The solid was washed with n-heptane, and dried for 24 hrs at 38° C. under vacuum to a drying loss of <1.0%, to obtain the crystal form A of TBN.

Figure 3:
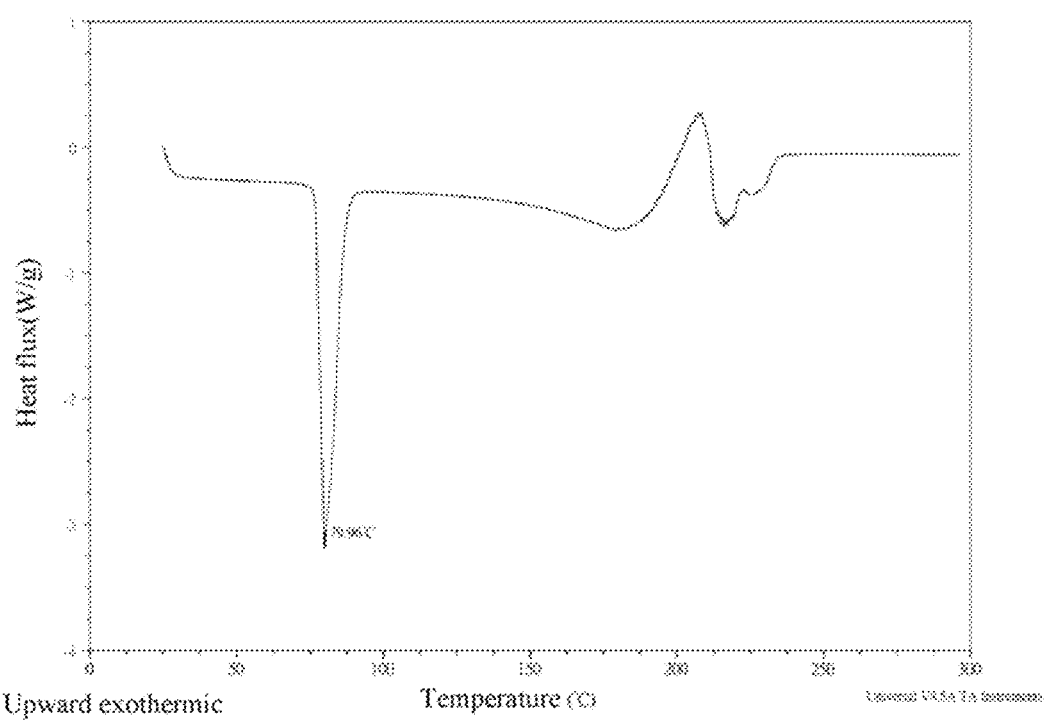
FIG. 3 shows an DSC pattern of the crystal form A of TBN.
Figure 5:
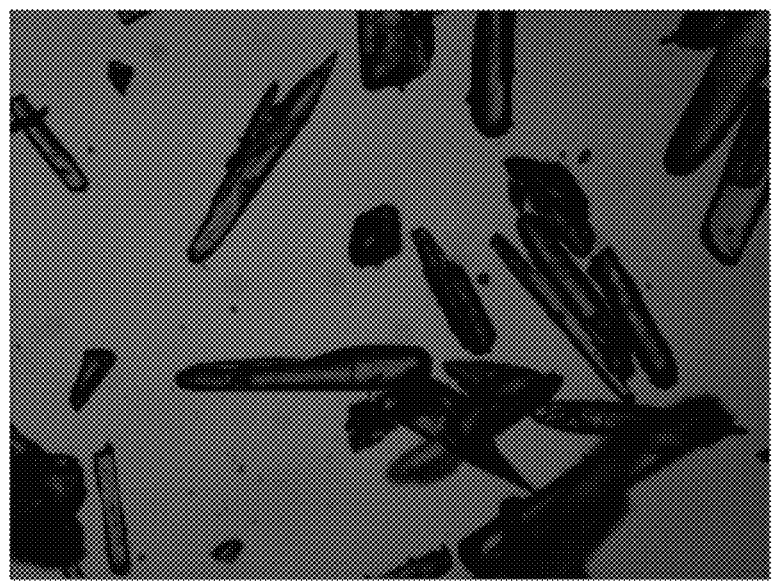
FIG. 5 shows a biological microscope image of the crystal form A of TBN.
Figure 6:
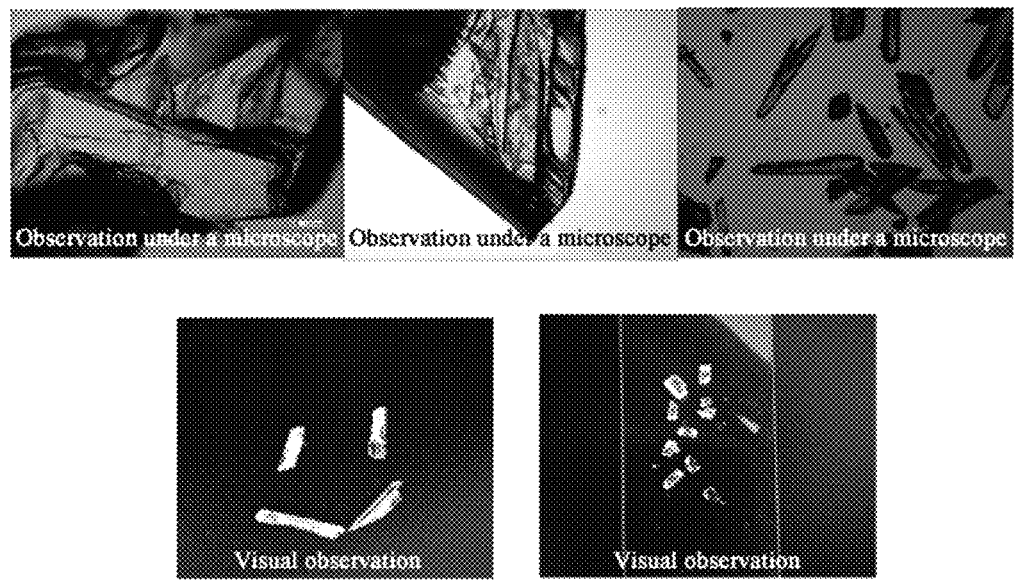
FIG. 6 shows the structure of the crystal form A of TBN.
Figure 7:
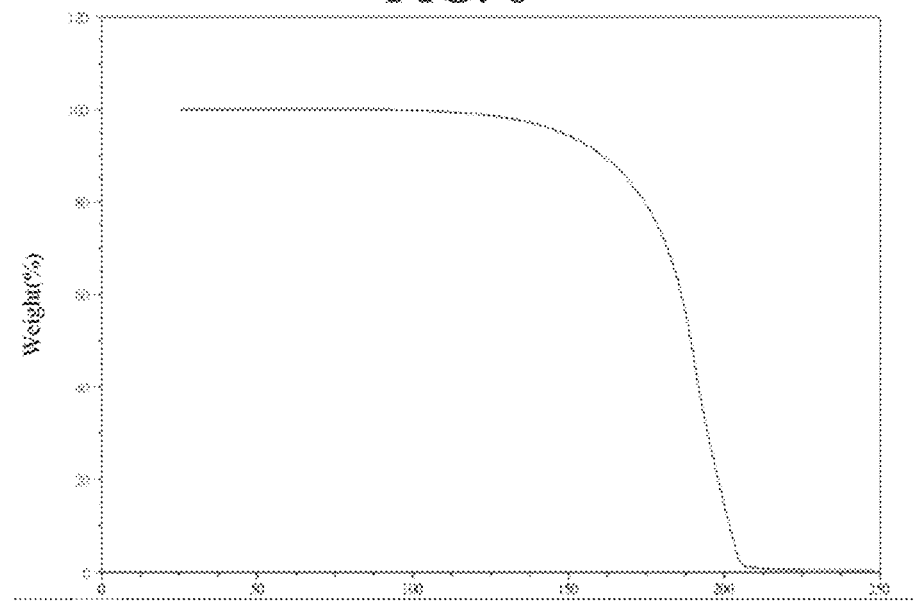
FIG. 7 shows an TGA pattern of the crystal form A of TBN.
Figure 9:
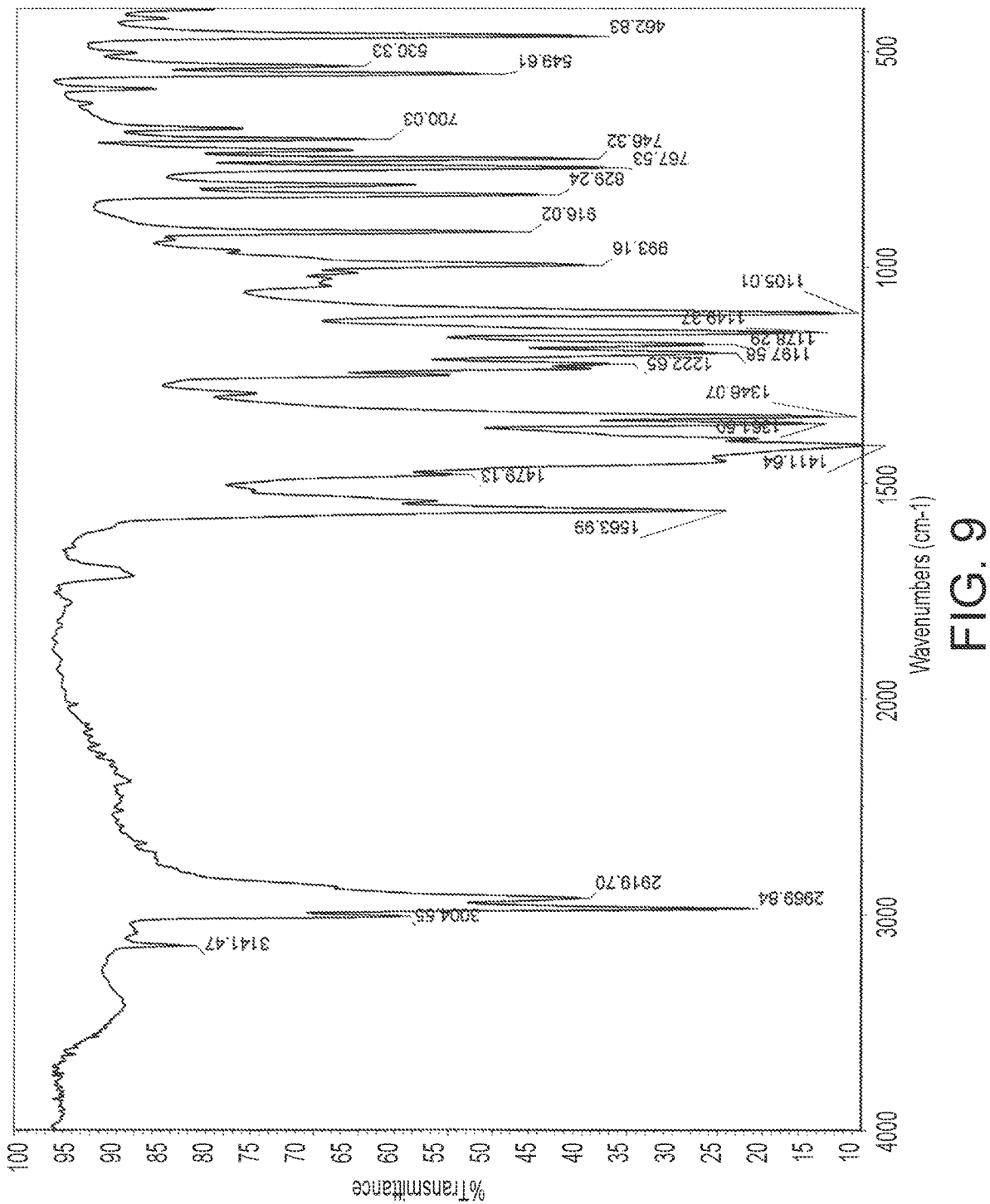
FIG. 9 shows an IR spectrum of the crystal form A of TBN.

The XRD pattern of the crystal form A of TBN prepared in Examples 1-7 is shown in FIG. 1 and Table 1. The crystal form A has characteristic diffraction peaks in the XRD pattern at 2θ°: 10.60±0.2, 11.03±0.2, 15.31±0.2, 15.55±0.2, 17.14±0.2, 17.93±0.2, and 23.81±0.2. The DSC profile is shown in FIG. 3, in which there is an endothermic peak, which is a melting peak, and the melting point is between 76-78° C. It can be seen from the micrographs of FIG. 5 and FIG. 6 that TBN has three crystalline structures, namely needle-, cube-, or rod-shaped crystalline structure. The TGA pattern is shown in FIG. 7. The IR spectrum is shown in FIG. 9.

Example 8

Figure 2:
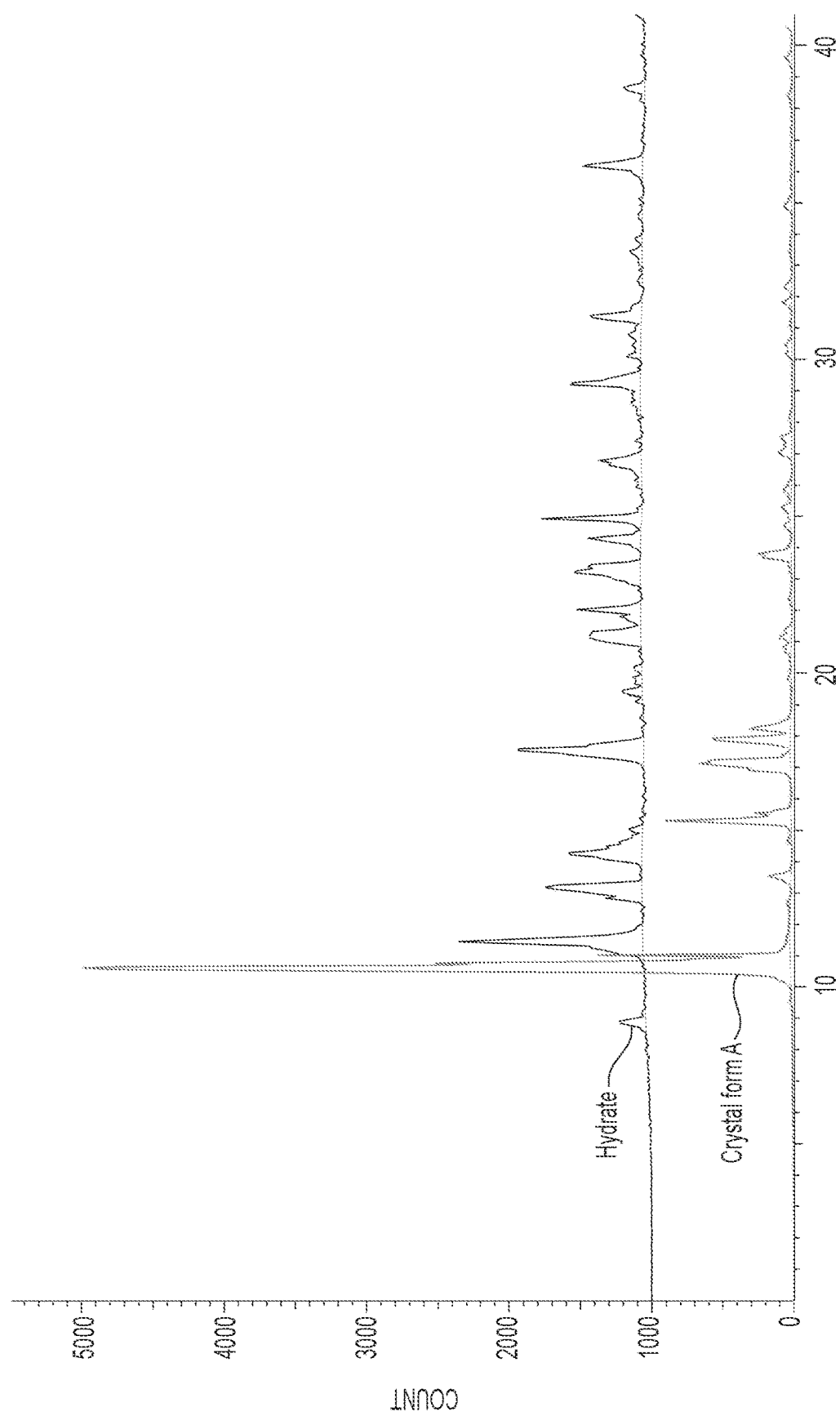
FIG. 2 compares XRD patterns of the crystal form A and dihydrate of TBN.
Figure 4:
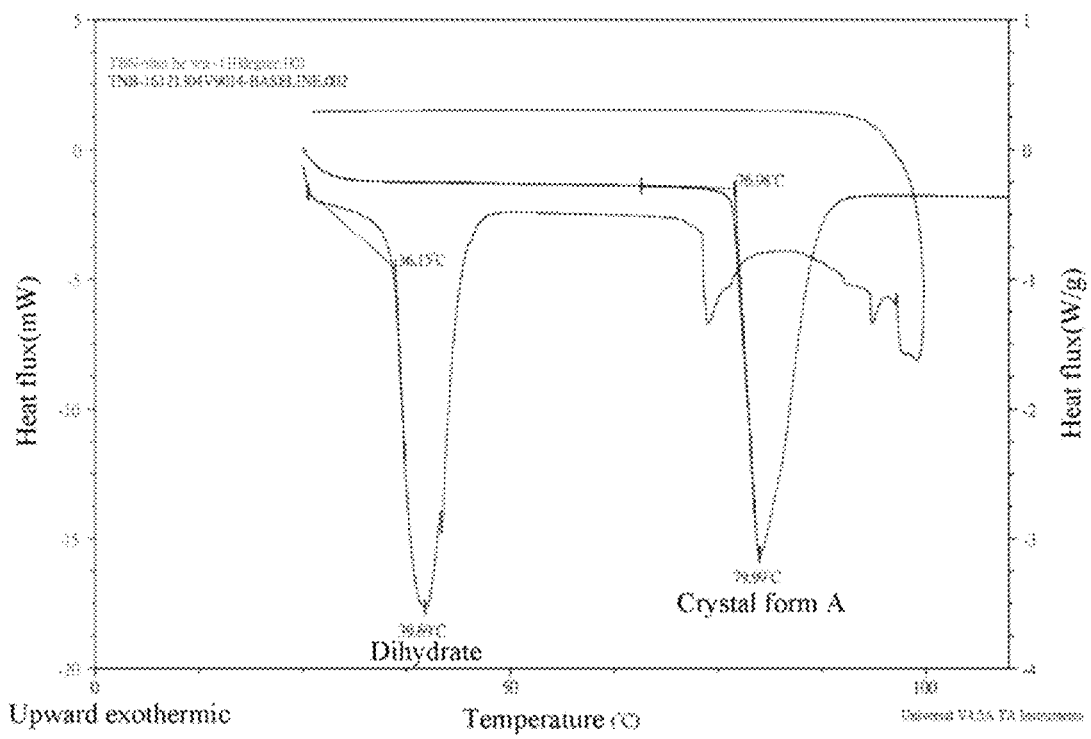
FIG. 4 shows a DSC profile of the crystal form A and dihydrate of TBN.
Figure 8:
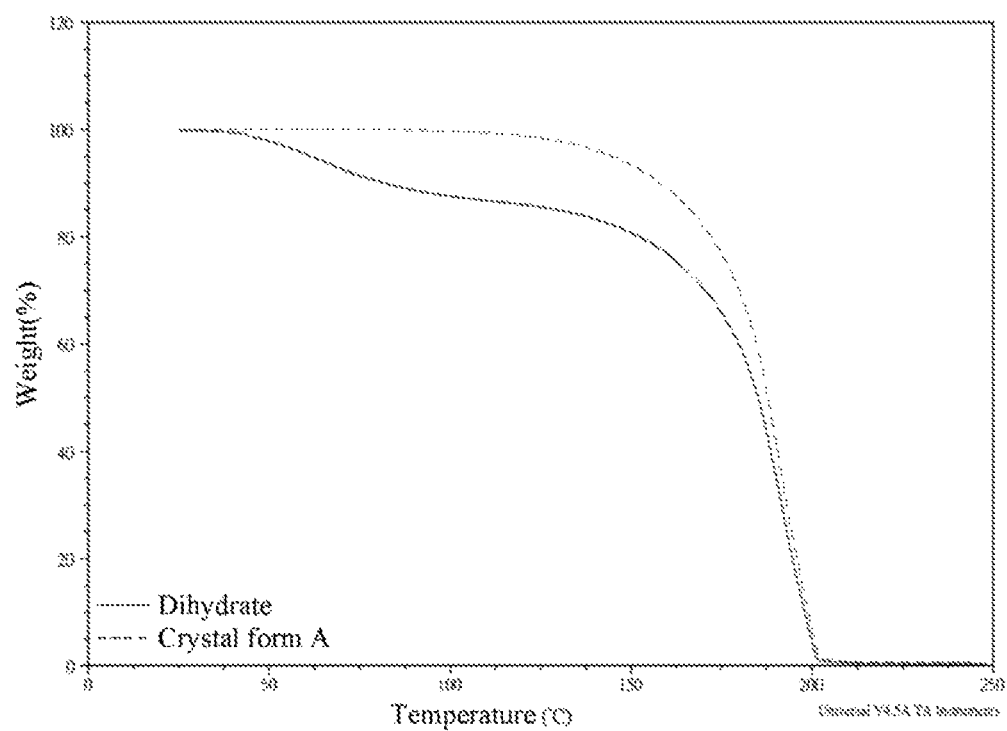
FIG. 8 compares TGA patterns of the crystal form A and dihydrate of TBN.

TBN is cold precipitated in a binary system of a saturated ethanol/water solution (9% ethanol by volume) to obtain a TBN dihydrate. The XRD pattern of the prepared dihydrate is shown in FIG. 2 and Table 1. The dihydrate has characteristic diffraction peaks in the XRD pattern at 2θ°: 8.91±0.2, 11.46±0.2, 14.29±0.2, 17.60±0.2, 21.19±0.2, 22.02±0.2, 23.19±0.2, 24.30±0.2, 24.92±0.2, 29.20±0.2, and 31.41±0.2. The DSC profile is shown in FIG. 4, and the melting point of the TBN dihydrate is between 37-40° C. The TGA pattern is shown in FIG. 8.

TABLE 1

Comparison of characteristic diffraction peaks of crystal form A and dihydrate

| Crystal form A | | | Dihydrate | | |
| --- | --- | --- | --- | --- | --- |
| Angle of diffraction 2θ | Interplanar spacing (Å) | Relative diffraction intensity (I/I$_0$%) | Angle of diffraction 2θ | Interplanar spacing (Å) | Relative diffraction intensity (I/I$_0$%) |
| 10.598 | 8.34060 | 100% | 8.905 | 9.92208 | 17.1% |
| 11.025 | 8.01902 | 27.5% | 11.459 | 7.71598 | 100% |
| 15.308 | 5.78352 | 18.2% | 14.289 | 6.19362 | 42.9% |
| 15.551 | 5.69347 | 5.4% | 17.602 | 5.03464 | 66.0% |
| 17.135 | 5.17075 | 13.4% | 21.191 | 4.18935 | 32.2% |
| 17.926 | 4.94414 | 11.5% | 22.019 | 4.03360 | 38.7% |
| 23.813 | 3.73355 | 5.1% | 23.192 | 3.83213 | 40.0% |
| | | | 24.296 | 3.66039 | 33.1% |
| | | | 24.918 | 3.57053 | 57.4% |
| | | | 29.197 | 3.05623 | 42.0% |
| | | | 31.405 | 2.84615 | 31.7% |

Investigation of Preparation Method
1. The influence of solvent on the yield and quality of final product TBN. The results are shown in Table 2:

TABLE 2

The influence of solvent on the yield and quality of final product TBN

| | Name | Amount (g) | | | | |
| --- | --- | --- | --- | --- | --- | --- |
| | | Example 1 | Example 2 | Example 3 | Example 4 | Example 5 |
| Experimental section: | API (TBN) | 10 g | 10 g | 10 g | 10 g | 10 g |
| | Ethyl acetate | 2 mL | 2 mL | 0 | 0 | 0 |
| | n-hexane | 0 | 100 mL | 0 | 100 mL | 0 |
| | n-heptane | 0 | 0 | 0 | 0 | 100 mL |
| | Cyclohexane | 100 mL | 0 | 100 mL | 0 | 0 |
| Conclusion | Area content (%) | 97.69% | 99.34% | 99.46% | 99.68% | 99.71% |
| | Highest impurity content | 0.65% | 0.17% | 0.37% | 0.09% | 0.16% |

2. The influence of crystallization temperature on the yield and quality of final product TBN. The results are shown in Table 3:

TABLE 3

The influence of crystallization temperature on the yield and quality of final product TBN

| | Name | Amount (g) | |
| --- | --- | --- | --- |
| | | Example 6 (10° C.) | Example 7 (4° C.) |
| Experimental section: | API (TBN) | 10 g | 10 g |
| | n-hexane | 100 mL | 100 mL |
| Conclusion | Area content (%) | 99.60% | 99.87% |
| | Yield | 58% | 62% |
| | Highest impurity content | 0.4% | 0.08% |

Figure 10:
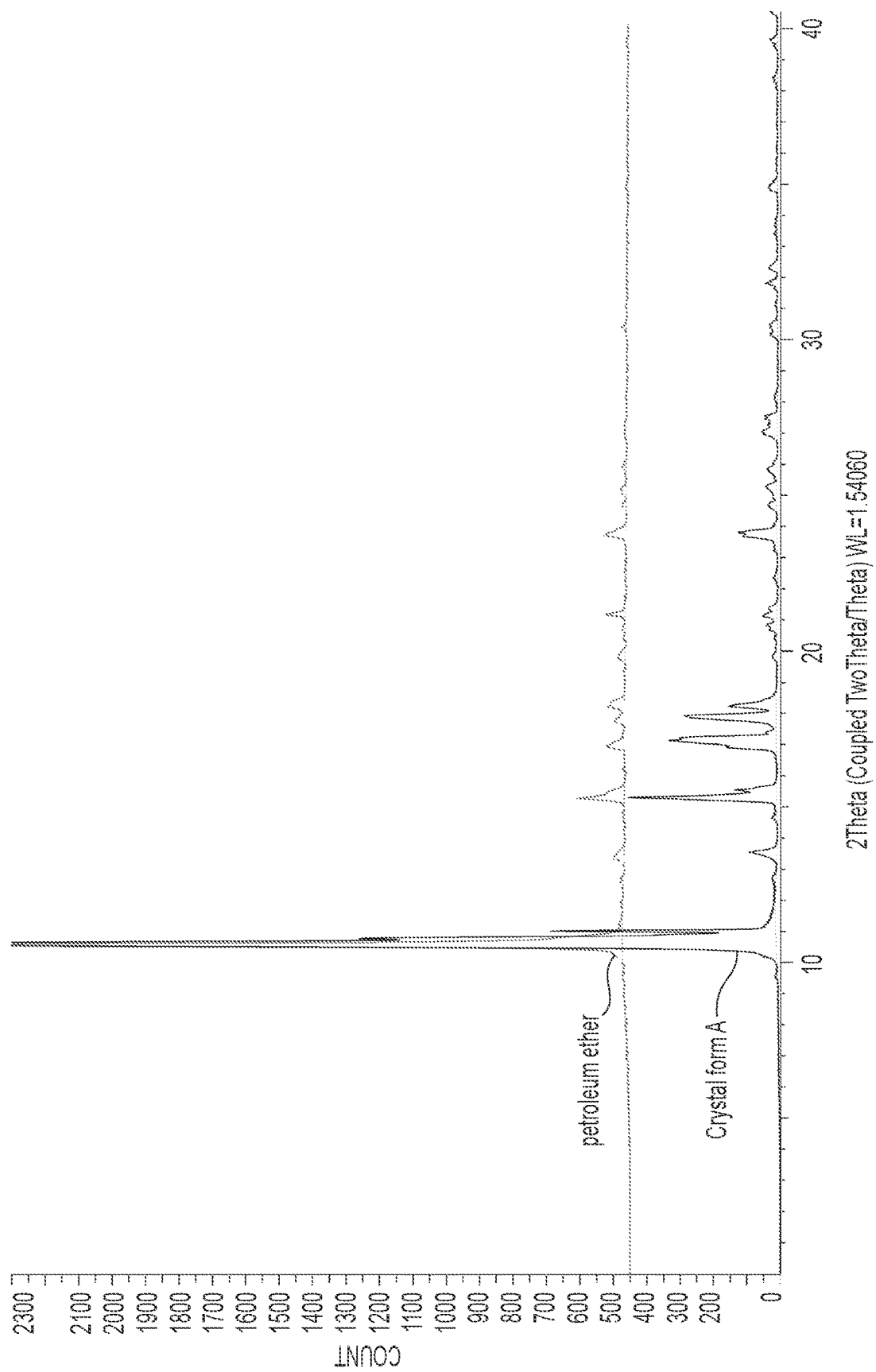
FIG. 10 shows an XRD pattern of the crystal form A of TBN one week after suspension beating.
Figure 11:
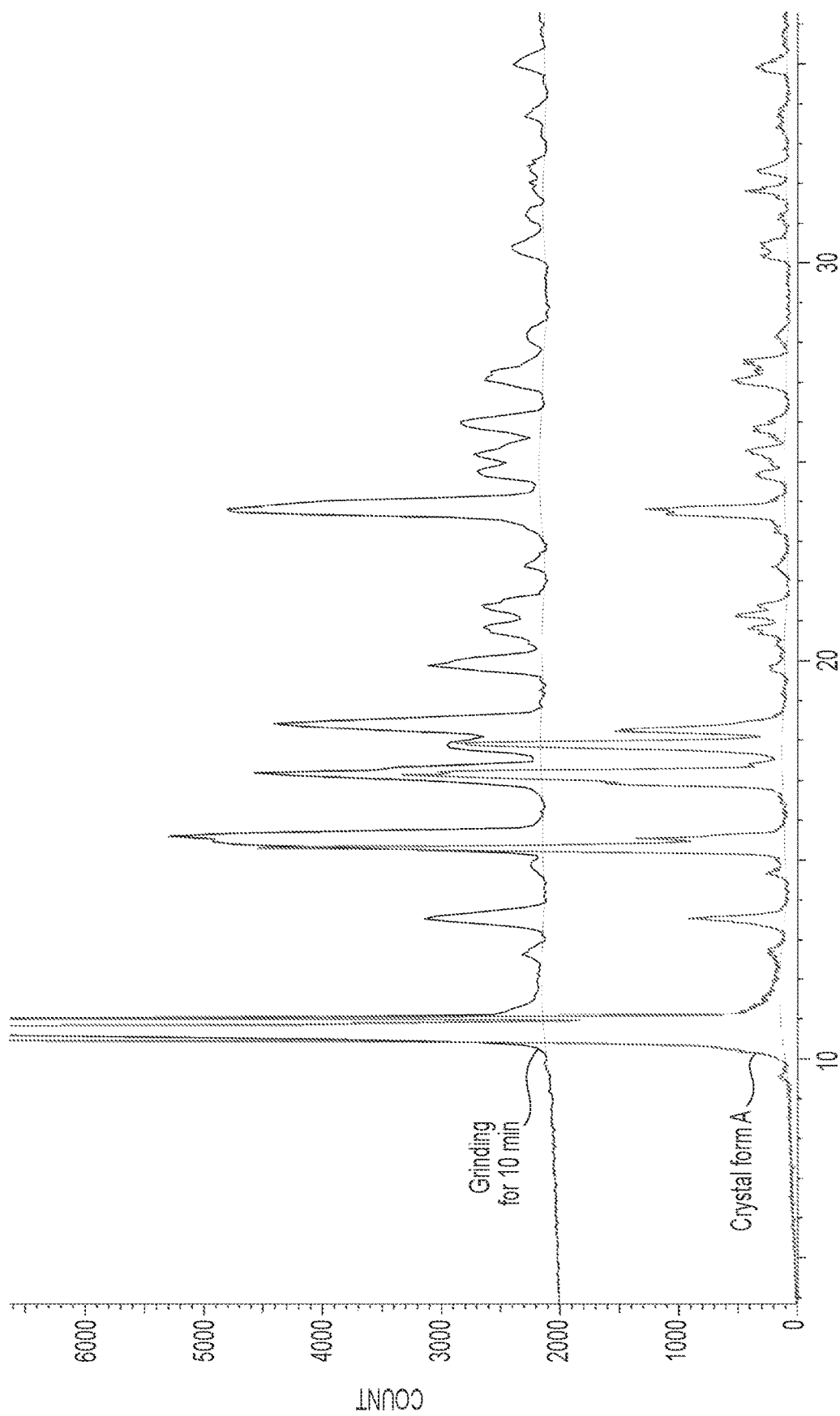
FIG. 11 shows an XRD pattern of the crystal form A of TBN after being ground for 10 min.
Figure 12:
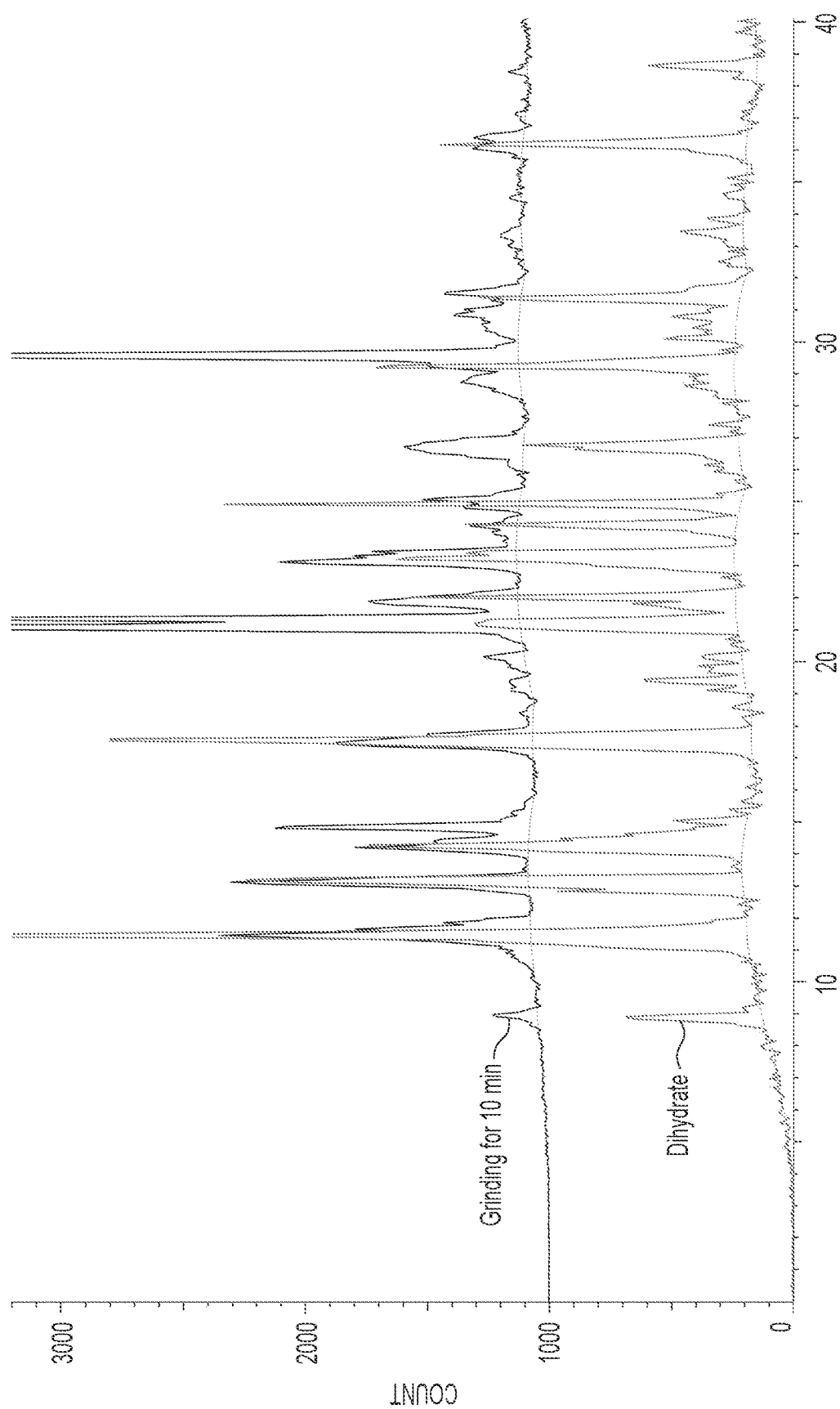
FIG. 12 shows an XRD pattern of the TBN dihydrate after being ground for 10 min.
Figure 13:
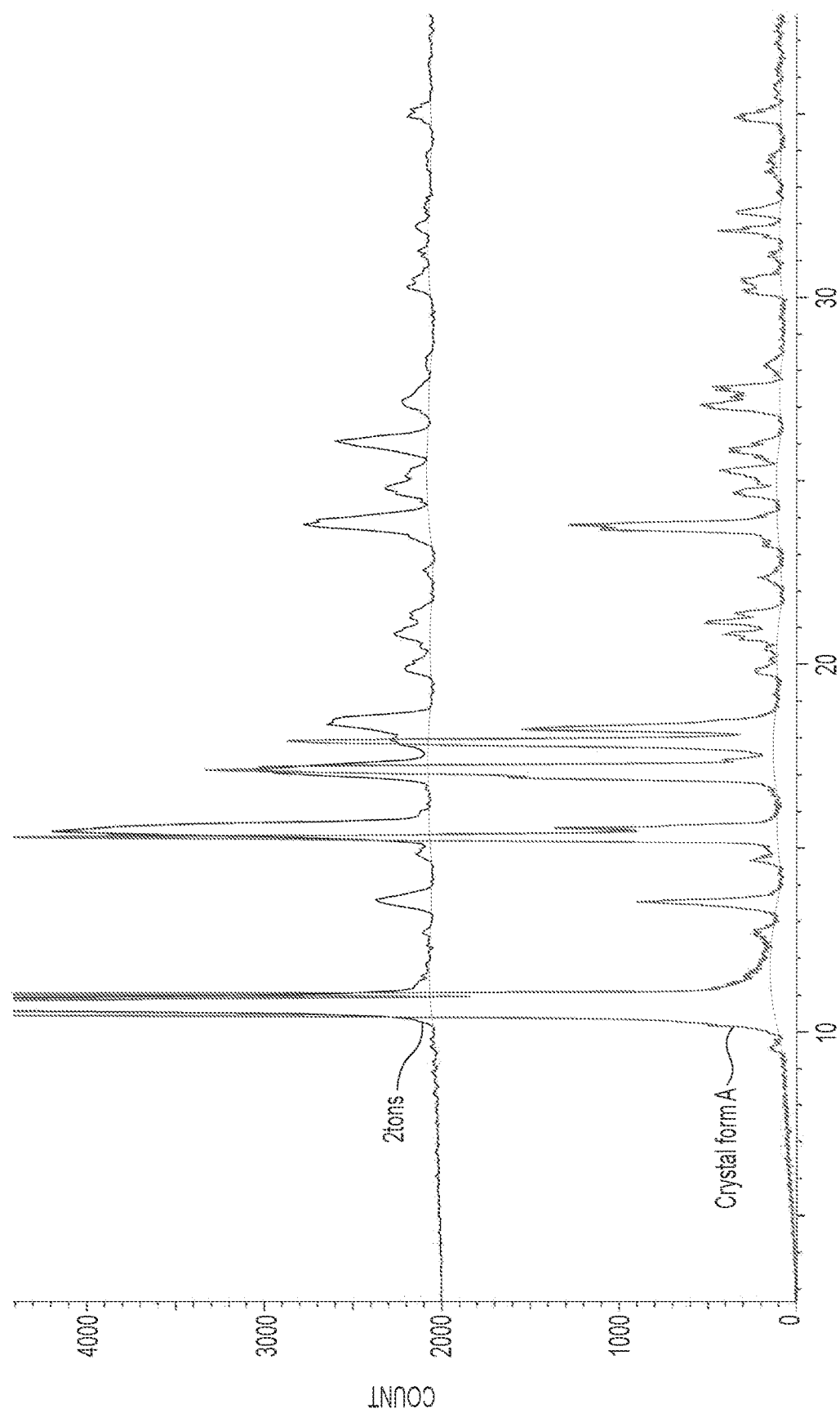
FIG. 13 shows an XRD pattern of the crystal form A after being tableted.
Figure 14:
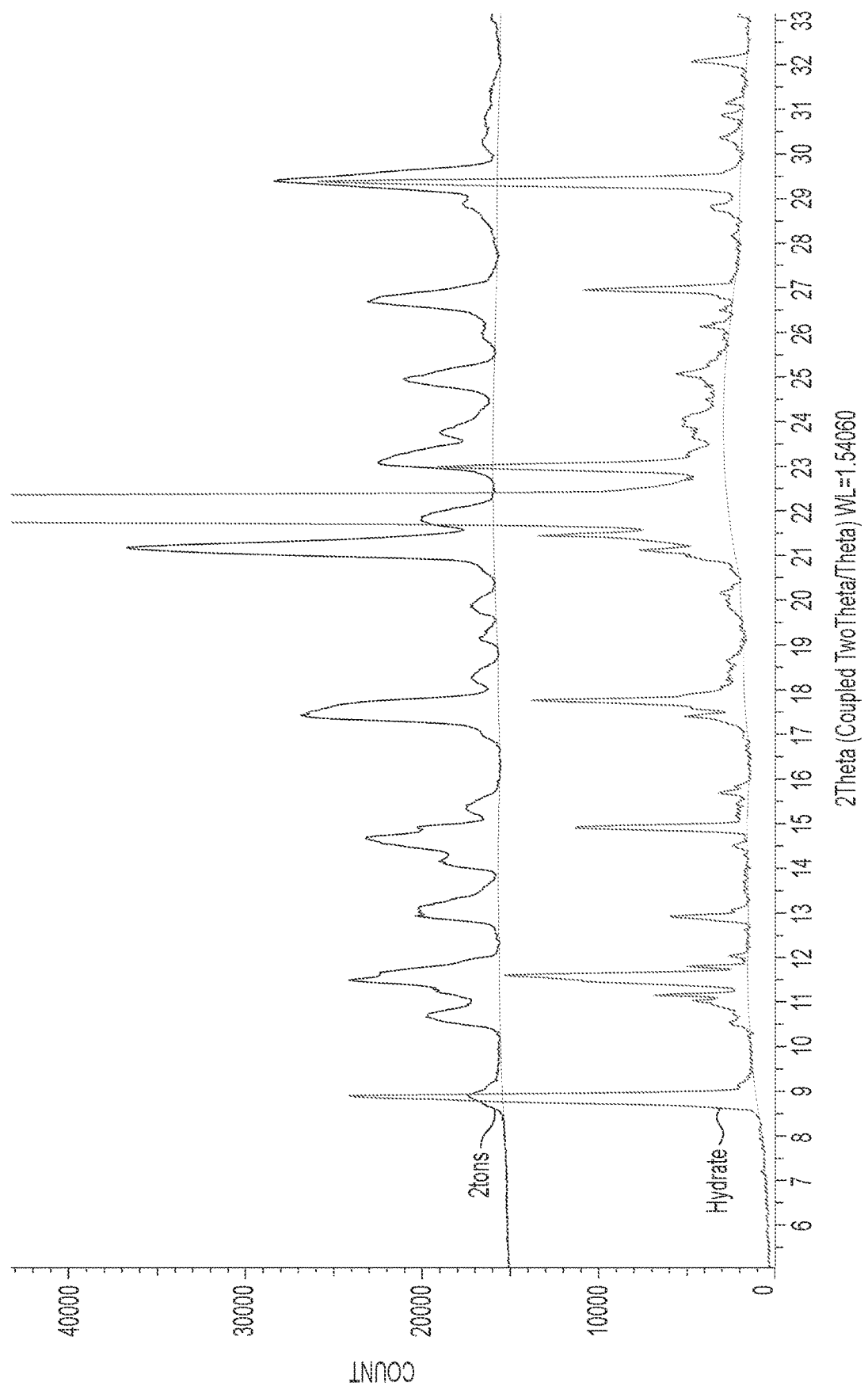
FIG. 14 shows an XRD pattern of the dihydrate after being tableted.
Figure 15:
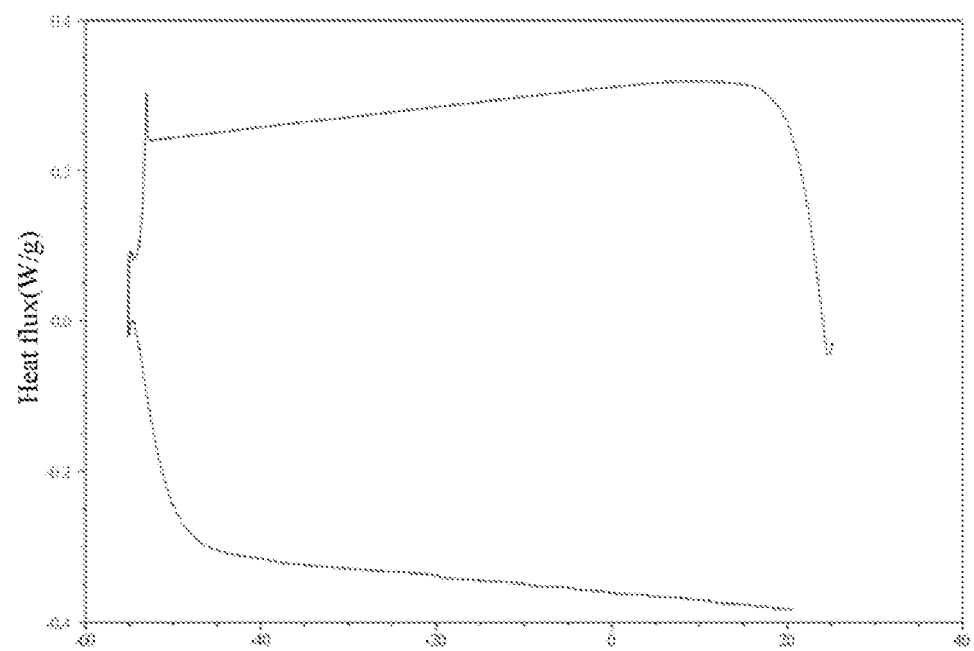
FIG. 15 shows a DSC profile of the crystal form A after a cooling treatment.
Figure 16:
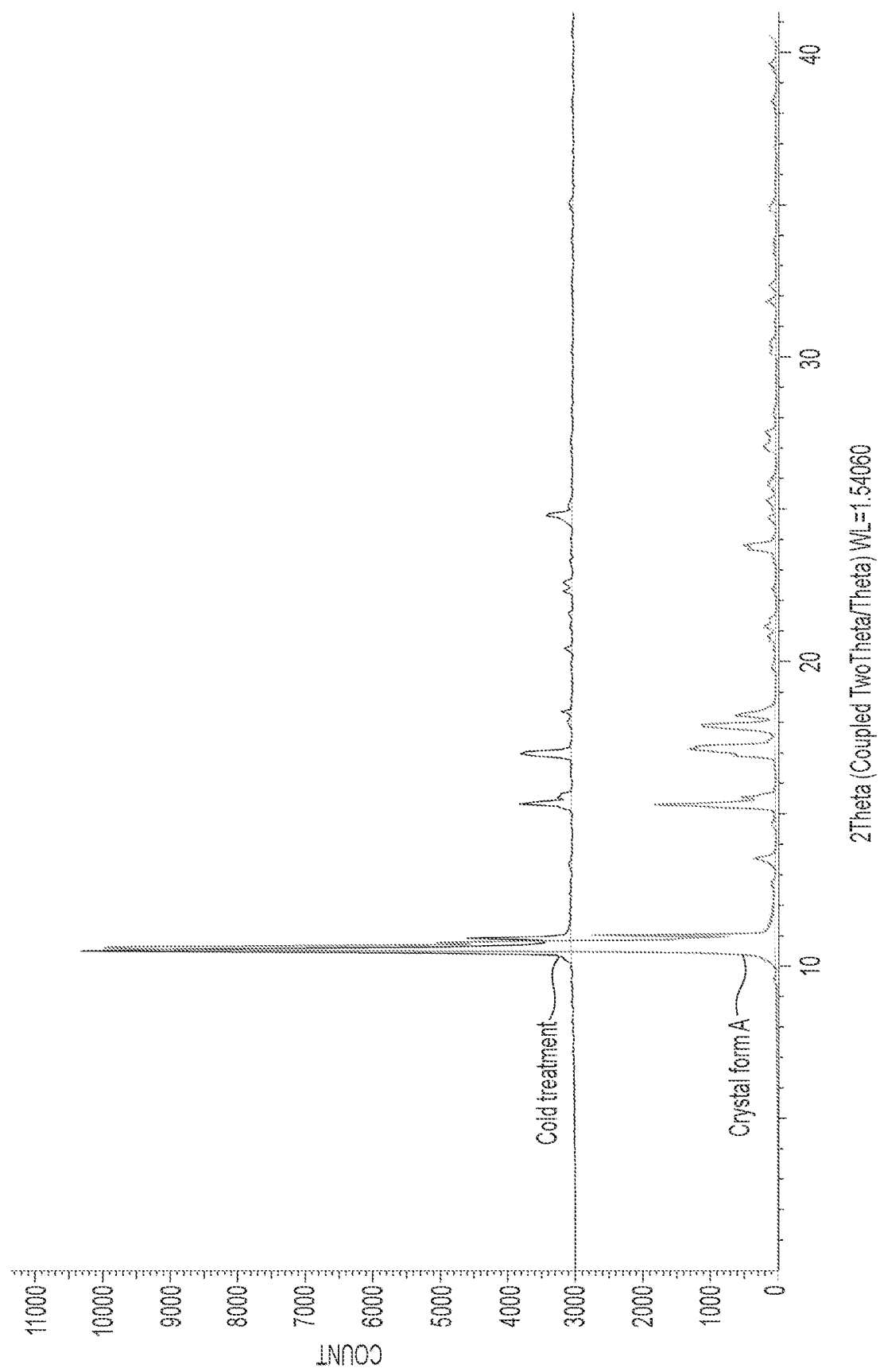
FIG. 16 shows an XRPD profile of the crystal form A after a cooling treatment.

Investigation of Performances:
1. Stability Investigation
1.1. Polymorph Transformation Test of Suspension
(1) The crystal form A of TBN was beaten in petroleum ether (1.0 mL) at room temperature for 7 days, and then the suspension was centrifuged, and the solid sample was collected for characterization by XRPD.
The results show that after the crystal form A of TBN is beaten in suspension in petroleum ether for a week, it is still crystal form A. The XRD pattern is shown in FIG. 10.
1.2. Test of Stability Against Mechanical Treatment
(2) The crystal form A of TBN and the TBN dihydrate were ground for 10 min receptively, and the treated samples were analyzed by XRPD.
The results show that the XRPD characteristic peaks of the crystal form A of the present invention have no change after grinding for 10 min. The crystal form of TBN dihydrate has no change after grinding for 10 min. The patterns are shown in FIG. 11 and FIG. 12.
1.3. Tableting Test
(3) The crystal form A and the TBN dihydrate were tableted under a pressure of 2 tons for 2 min. The tablets thus obtained were analyzed by XRPD.
The results show that the crystal form A and the TBN dihydrate do not undergo polymorph transformation after 2 min of pressurization under 2 tons (where the crystallinity became smaller), as shown in FIGS. 13 and 14.
1.4. Test of Stability Against Cold/Heat Treatment
(4) The crystal form A was cooled to −55° C., and then heated to 25° C. The results show that the crystal form A does not undergo polymorph transformation, as shown in FIGS. 15 and 16.

Figure 17:
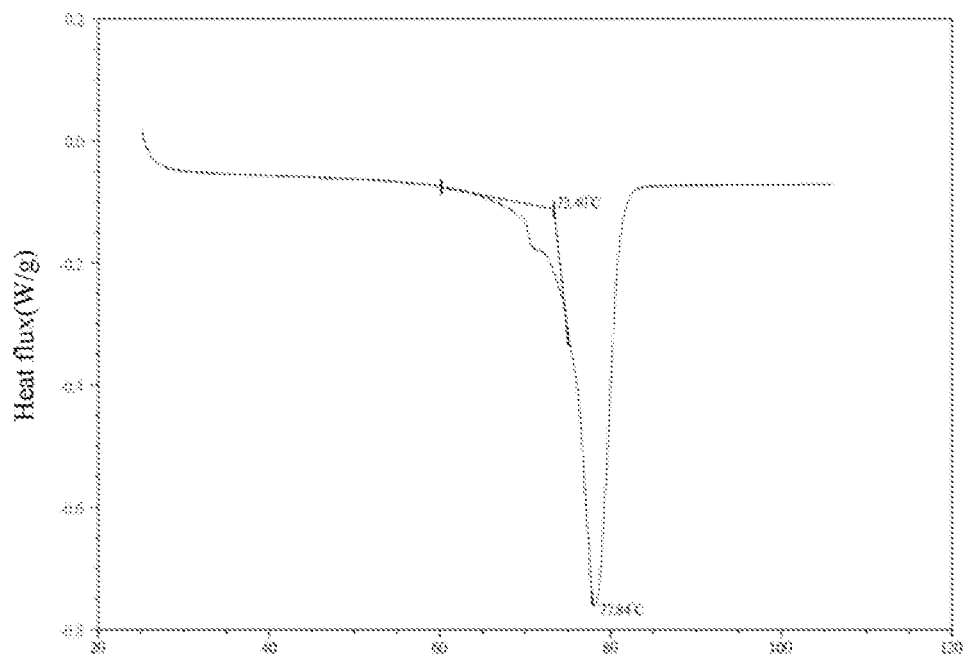
FIG. 17 shows a DSC profile of the crystal form A after thermal treatment 1.
Figure 18:
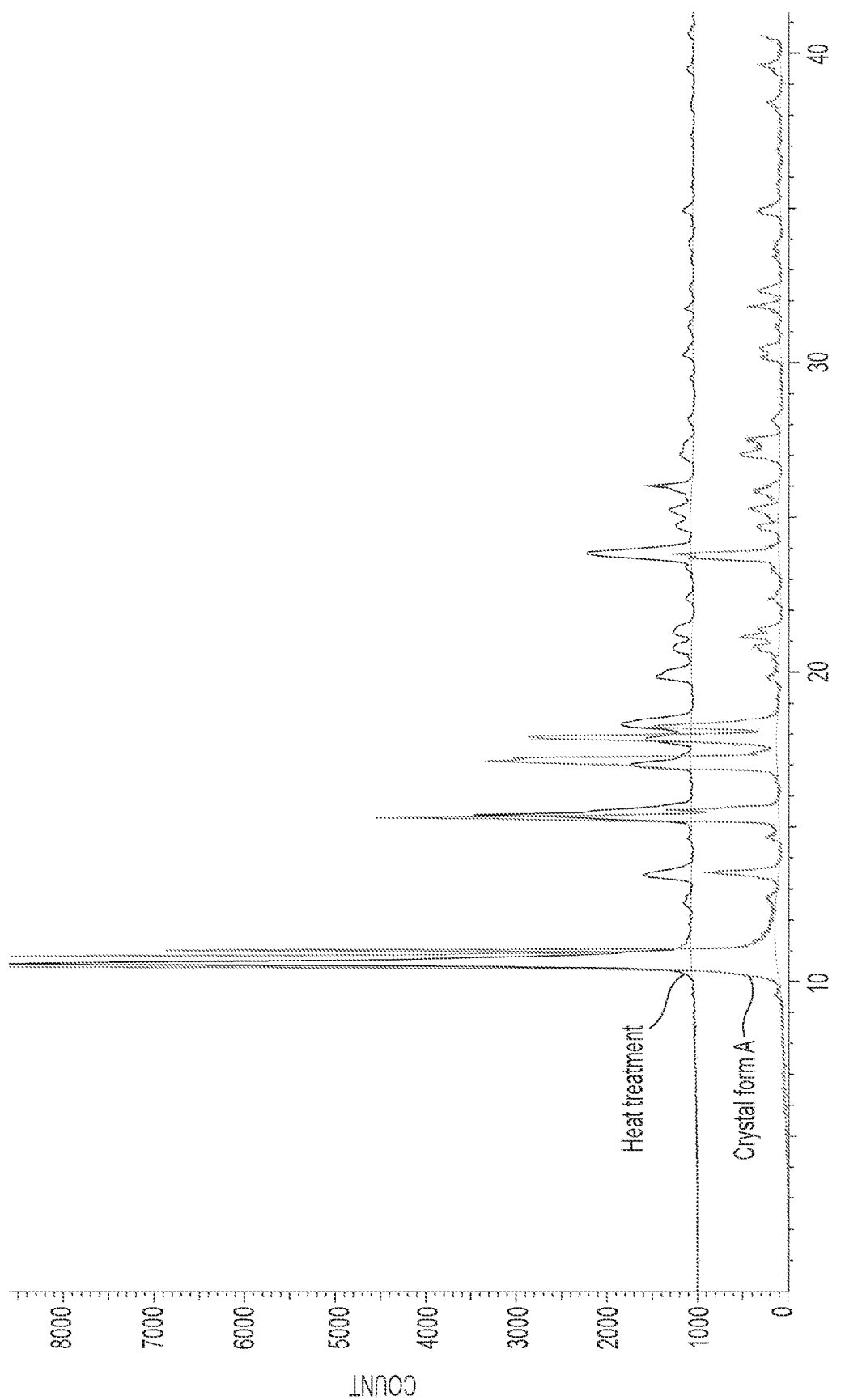
FIG. 18 shows an XRPD profile of the crystal form A after thermal treatment 1.

(5) The crystal form A was heated to 110° C. (before the decomposition point), and then cooled to 25° C. to obtain a yellow oily liquid. After stirring, a white solid was precipitated out, which is characterized by XRPD as crystal form A, as shown in FIGS. 17 and 18.

Figure 19:
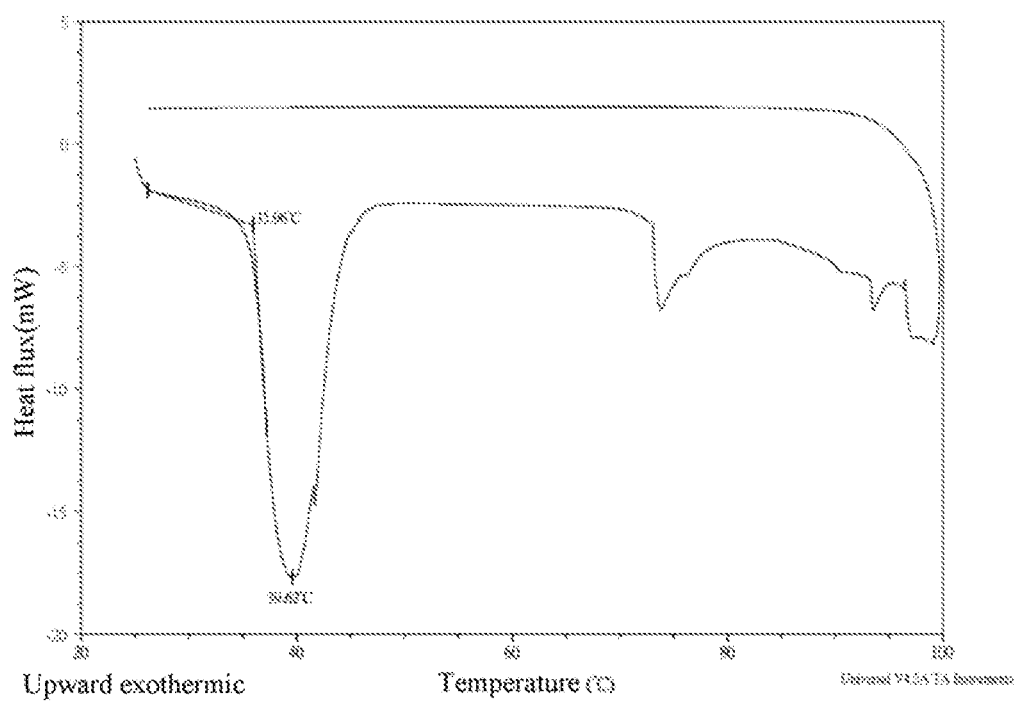
FIG. 19 shows a DSC profile of the TBN dihydrate after a thermal treatment.
Figure 20:
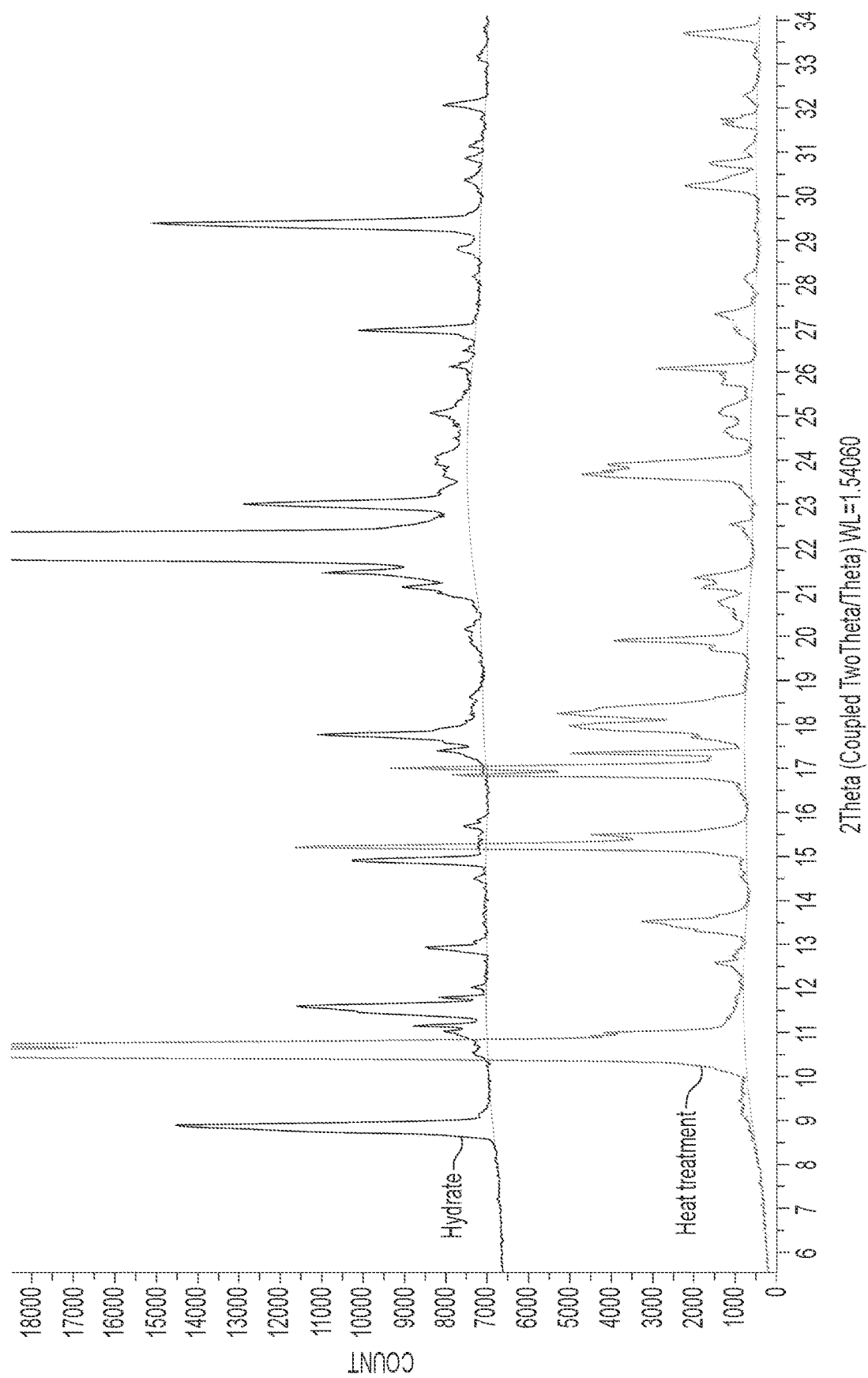
FIG. 20 shows an XRPD profile of the TBN dihydrate after a thermal treatment.

(6) The TBN dihydrate was heated to 110° C. (before the decomposition point), and then cooled to 25° C. to obtain a yellow oily liquid. After stirring, a white solid was precipitated out, which is characterized by XRPD as crystal form A, as shown in FIGS. 19 and 20.

1.5. Test of Influence of Acceleration

Figure 21:
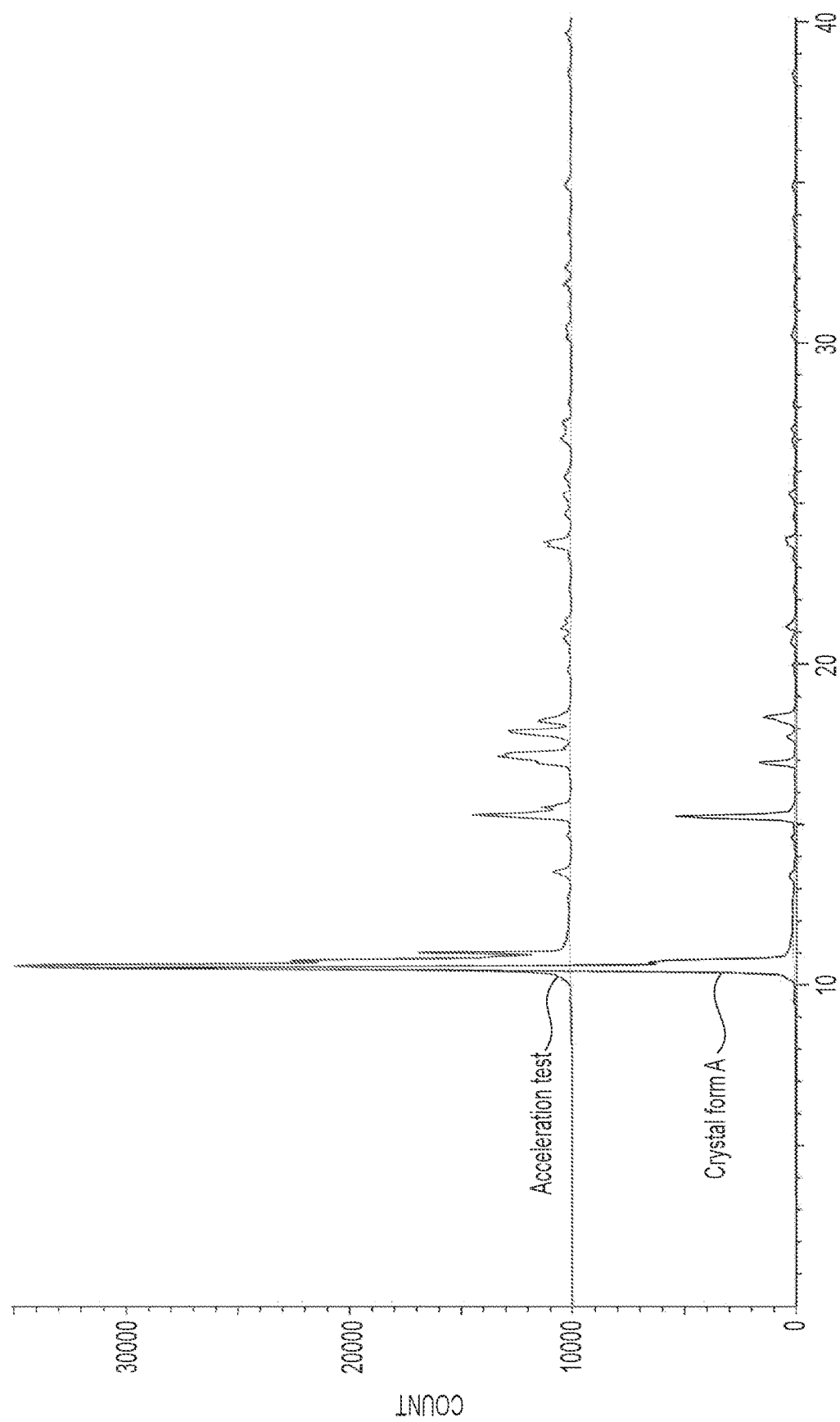
FIG. 21 shows an XRPD profile of the crystal form A after 7 days of acceleration test.

When the crystal form A is accelerated for 7 days at 40° C. and RH=75%, the XRPD characterization result shows crystal form A, as shown in FIG. 21.

2. Investigation of Biological Activity

The pharmacodynamic study in cynomolgus monkey animal model of cerebral stroke and also the pharmacokinetic study of the crystal form A of TBN in the cerebrospinal fluid of cynomolgus monkey were carried out. 10 min, 30 min, 60 min, and 120 min after the second administration (30 mg/kg, 6 hrs after the first intravenous administration of 30 mg/kg), 0.5 ml of cerebrospinal fluid was collected for pharmacokinetic test.

TABLE 4

Drug concentration-time data in cerebrospinal fluid of cynomolgus monkeys given TBN at 30 mg/kg intravenously

| Route of administration | Animal No. | TBN at various time (min) | | Drug concentration in cerebrospinal fluid (ng/ml) | |
|---|---|---|---|---|---|
| | | 10 | 30 | 60 | 120 |
| Intravenous injection | Monkey-080135 | 34300 | 25100 | 20000 | 7800 |
| | Monkey-070361 | 48800 | 41100 | 27500 | 16500 |
| | Monkey-071515 | 33700 | 32200 | 25300 | 14300 |

The test results in Table 4 show that 10 min after the second administration, the concentration of TBN in the cerebrospinal fluid is 176 μM, which is almost equal to the concentration of the drug in plasma (195 μM), and higher than the effective protection concentration of 30 μM of TBN in in vitro cell experiments. This result shows that the crystal form A of TBN penetrate through the blood-brain barrier and reach an effective protection concentration.

3. Metabolic Data: Clearance Rate

SD rats were given the crystal form A of TBN at a dose of 30 mg/kg by intravenous injection and the distribution of the crystal form A of TBN in various tissues was investigated.

Figure 22:
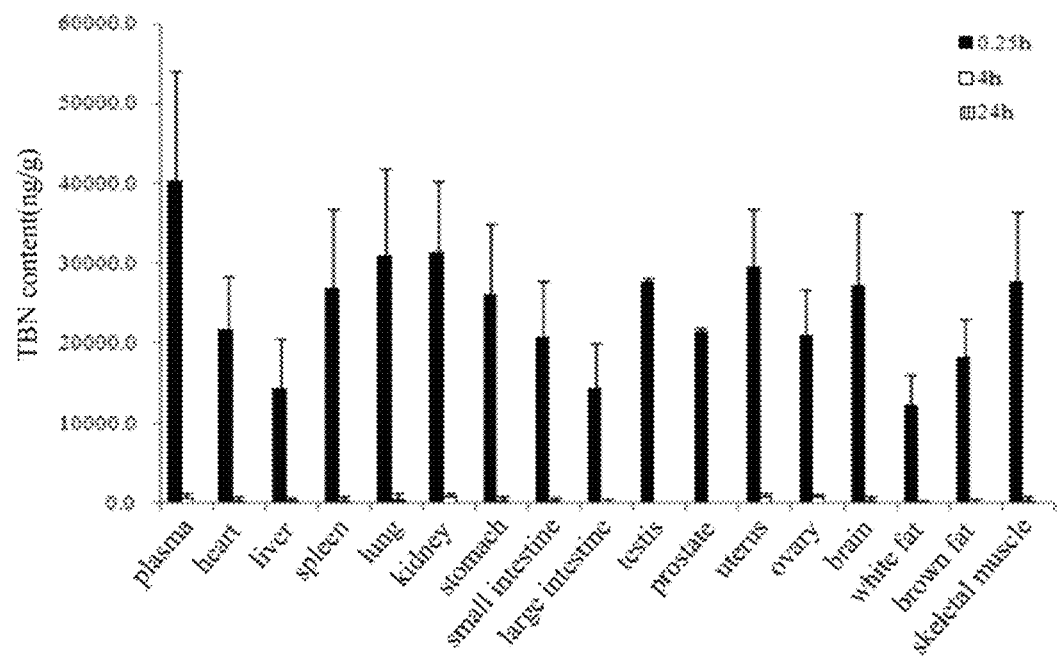
FIG. 22 shows the distribution in tissues after intravenous administration of TBN (30 mg/kg, n=6, male:female 1:1) to SD rats.

The experimental results are shown in FIG. 22. The results show that after intravenous administration of TBN to female and male rats at 30 mg/kg, rapid and widespread distribution is reached in all tissues and plasma almost at the same time, and the drug is cleared away from the tissues and plasma almost at the same time in 24 hrs. TBN does not tend to accumulate in the detected tissues. 0.25 hrs after administration, the concentration of TBN in the brain tissue is 0.6-0.7 time the plasma concentration, and 0.8-1.1 times the plasma concentration after 4 hrs, and TBN is completely cleared as is in the plasma at 24 hrs.

What is claimed is:

1. A crystal form A of tetramethylpyrazine nitrone (TBN) wherein the crystal form A is characterized by an X-ray powder diffraction (XRPD) pattern having peaks at degrees 2θ of: 10.60±0.2, 11.03±0.2, 15.31±0.2, 15.55±0.2, 17.14±0.2, 17.93±0.2, and 23.81±0.2.

2. The crystal form A of TBN according to claim 1, wherein the XRPD pattern has peaks at degrees 2θ of: 10.60±0.2, 11.03±0.2, 13.51±0.2, 15.31±0.2, 15.55±0.2, 17.14±0.2, 17.93±0.2, 21.22±0.2, 23.81±0.2, 25.23±0.2, and 27.08±0.2.

3. The crystal form A of TBN according to claim 1, wherein the crystal form A has a melting point that is in the range of from 76-78° C.

4. A method for preparing the crystal form A according to claim 1, comprising the following steps:
   (1) mixing active pharmaceutical ingredient (API) TBN with an organic solvent, heating in a water bath to 60-80° C., stirring and filtering, and cooling the filtrate for crystallization to obtain a crystalline solid; and
   (2) mixing the crystalline solid obtained in Step (1) and n-heptane, heating to dissolve it, and cooling for crystallization to obtain the crystal form A of TBN.

5. The preparation method according to claim 4, wherein the organic solvent in Step (1) is one or more selected from ethyl acetate, n-hexane, n-heptane and cyclohexane; the weight-to-volume ratio of the API TBN to the organic solvent in Step (1) is 1:5-20; the temperature of cooling for crystallization in Step (1) is 2-12° C.; the weight-to-volume ratio of the API TBN to n-heptane in Step (2) is 1:1-5; the mixing and heating temperature of the crystalline solid and n-heptane in Step (2) is 60-80° C.; and the temperature of cooling for crystallization in Step (2) is 2-12° C.

6. A tetramethylpyrazine nitrone (TBN) dihydrate, wherein the TBN dihydrate is characterized by an X-ray powder diffraction (XRPD) pattern having peaks at degrees 2θ of: 8.91±0.2, 11.46±0.2, 14.29±0.2, 17.60±0.2, 21.19±0.2, 22.02±0.2, 23.19±0.2, 24.30±0.2, 24.92±0.2, 29.20±0.2, and 31.41±0.2.

7. The TBN dihydrate according to claim 6, wherein the TBN dihydrate has a melting point that is in the range of from 37-40° C.

8. A pharmaceutical composition, comprising the crystal form A according to claim 1 and one or more pharmaceutically acceptable excipients.

9. A pharmaceutical composition, comprising the TBN dihydrate according to claim 6 and one or more pharmaceutically acceptable excipients.

10. The TBN dihydrate according to claim 6, wherein the XRPD pattern has peaks at degrees 2θ of: 8.91±0.2, 11.46±0.2, 12.00±0.2, 14.29±0.2, 17.60±0.2, 19.50±0.2, 21.19±0.2, 22.02±0.2, 23.19±0.2, 24.30±0.2, 24.92±0.2, 26.70±0.2, 29.20±0.2, 31.41±0.2, and 36.20±0.2.

* * * * *